Figure 1:
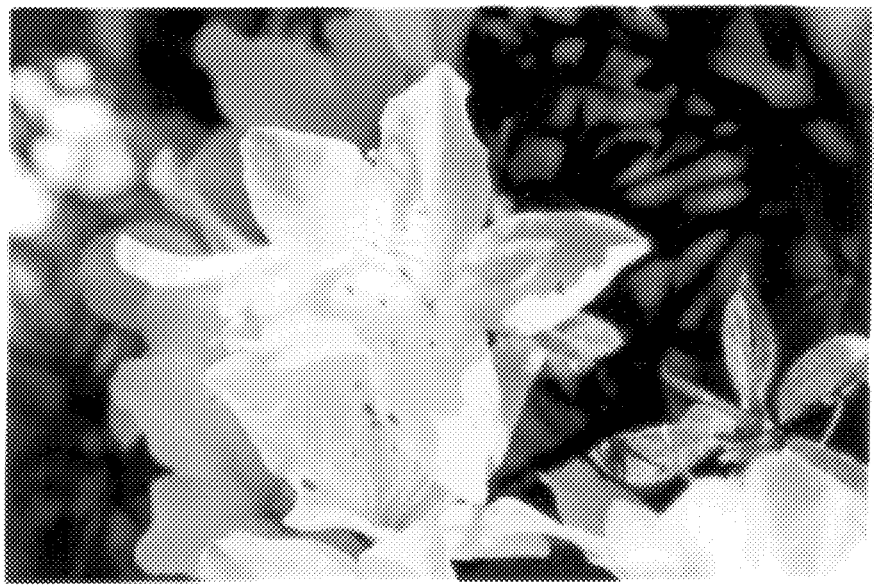
Figure 2:
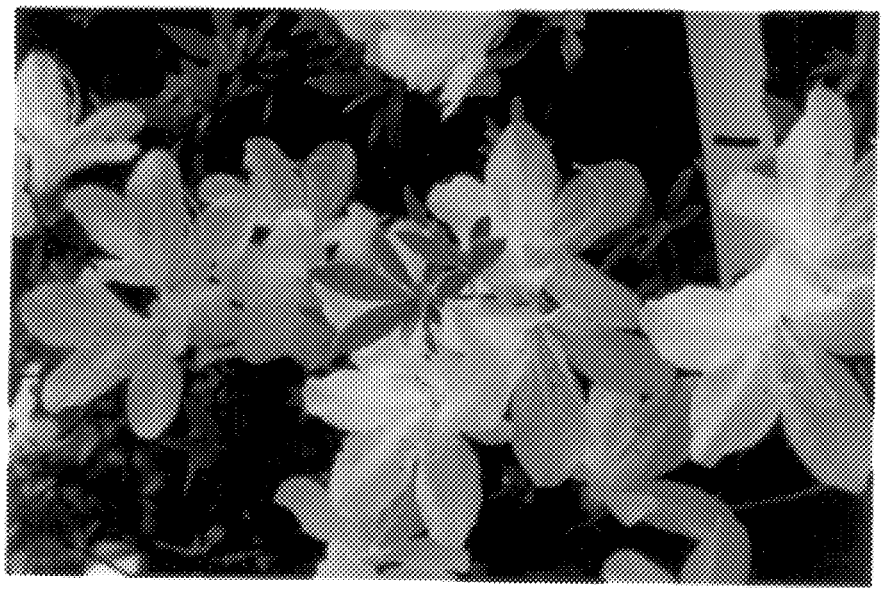
Figure 3:
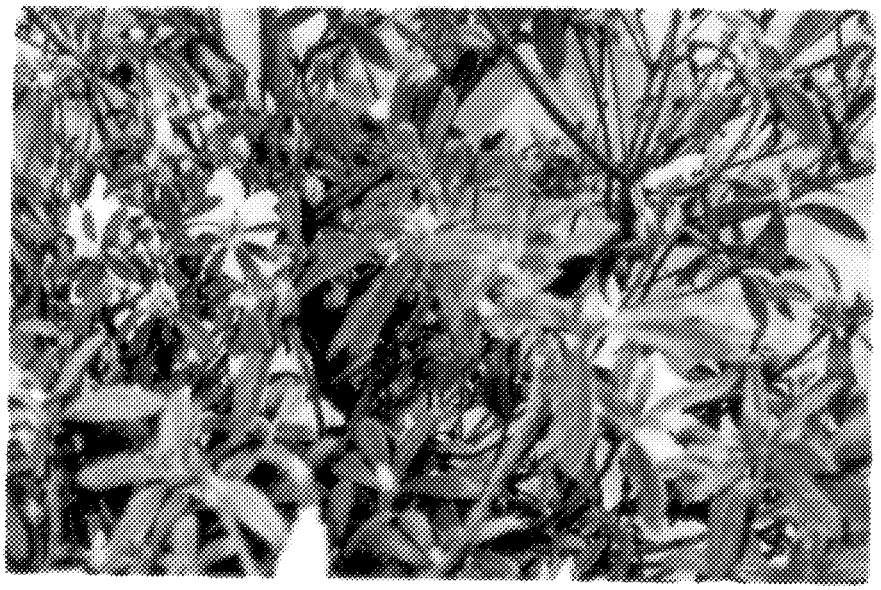

US00PP10467P

United States Patent [19]

Johnson

[11] Patent Number: Plant 10,467

[45] Date of Patent: Jun. 30, 1998

[54] AZALEA PLANT NAMED 'CALVARY'S LOVE'

[76] Inventor: Elizabeth T. Johnson, 205 Thomas Rd., Clover, S.C. 20710

[21] Appl. No.: 805,219

[22] Filed: Feb. 27, 1997

[51] Int. Cl.[6] ..... A01H 5/00

[52] U.S. Cl. ..... Plt./55

[58] Field of Search ..... Plt./55

*Primary Examiner*—Elizabeth C. Kemmerer
*Attorney, Agent, or Firm*—Christie, Parker & Hale, LLP

[57] ABSTRACT

An azalea plant variety producing unmarked white flowers.

2 Drawing Sheets

BACKGROUND OF THE INVENTION

The present invention relates to a new and distant variety of evergreen azalea of the genus Rhododendron and a member of the ericaceae family. The new variety is a plant from seed harvested from a plant of Southern Indian azalea. The specific parentage of the new variety is unknown.

SUMMARY OF THE INVENTION

The new variety is distinguished by unmarked pure white flowers without splotches or discolorations common to other varieties of white flowered azaleas. Plants and buds of the new variety are hardy to at least 0°F. and in Zone 7A and 7B and flower in early April.

Asexual reproduction of the new variety by vegetative cuttings in Clover, S.C., has demonstrated that the distinguishing characteristics are retained in successive propagations. The varietal denomination of the new variety is 'Calvary's Love'.

BRIEF DESCRIPTION OF ILLUSTRATION

The accompanying illustrations show specimens of the variety as grown in Clover, S.C., with coloration being as true as possible in color illustrations of this type. Phenotypic expression may vary with environmental, growing, and climatic conditions.

One of the accompanying illustrations depicts the pure white flowers of the new variety; a second illustration shows the white flowers and juvenile foliage and a third illustration shows foliage and buds of a mature plant.

DESCRIPTION OF THE NEW VARIETY

The following is a detailed description of the new variety, of plants grown in Clover, S.C. Color values are described in terms of The Royal Horticultural Society Colour Chart (RHSCC).

Botanical classification:
- *Family*.—Ericacae.
- *Genus*.—Rhododendron.

Origin: Hybrid seedling.

Parentage: Unknown.

Plant:
- *Form*.—Shrub.
- *Size* (*mature plant*):—About 4 to 6 feet tall, about 6 to 8 feet wide.
- *Habit*.—Intermediate foliage density.
- *Foliage*.—Juvenile foliage: Near 147C. Mature foliage: Near 133B to 133C. Leaf size: About 2¼ inches long, about ⅝ inches wide. Leaf shape: Elliptic, flat. Leaf base: Cuneate. Leaf tip; Acute. Leaf surface: Semi-glossy. Indumentum: Discrete hairs.
- *Stems*.—Brown to brownish gray.

Bud:
- *Form*.—Ovate, pointed.
- *Size*.—About ¼ to ¾ inches long; about ¼ to ½ inch wide.
- *Color*.—Near 138D to 140D, opening yellowing white.
- *Calyx*.—About 0.4 inches long, light yellowish green.

Flowers:
- *Number per truss*.—About 2 to 3/terminal.
- *Shape*.—Broadly funnel-shaped.
- *Size*.—About 2.5 inches long, about 3 inches wide.
- *Lobes*.—Flat to very slightly wavy-edged lobes.
- *Color*.—Pure white, near 155D inside and outside; unmarked, no blotches or spots.
- *Corolla*.—Generally gamopetalous; fused at base.
- *Texture*.—Soft and delicate.

Reproduction organs:
- *Stamens*.—Long, about 4 to 8, white filaments.
- *Anthers*.—Deep pink.

What is claimed is:

1. A new and distinct azalea plant variety substantially, as shown and described.

* * * * *